US006245087B1

(12) United States Patent
Addis

(10) Patent No.: US 6,245,087 B1
(45) Date of Patent: Jun. 12, 2001

(54) VARIABLE EXPANSION FRAME SYSTEM FOR DEPLOYING MEDICAL DEVICES AND METHODS OF USE

(75) Inventor: Bruce Addis, Redwood City, CA (US)

(73) Assignee: Embol-X, Inc., Mountain View, CA (US)

(*) Notice: Subject to any disclaimer, the term of this patent is extended or adjusted under 35 U.S.C. 154(b) by 0 days.

(21) Appl. No.: 09/365,991

(22) Filed: Aug. 3, 1999

(51) Int. Cl.[7] .......................... A61M 29/00; A61B 17/22
(52) U.S. Cl. ................................. 606/200; 606/159
(58) Field of Search .............................. 606/200, 108, 606/194, 170, 159; 604/96, 104–106, 95

(56) References Cited

U.S. PATENT DOCUMENTS

| 4,650,466 | * | 3/1987 | Luther | 604/95 |
| 5,662,671 | * | 9/1997 | Barbut et al. | 606/170 |
| 5,848,964 | * | 12/1998 | Samuels | 606/200 |
| 5,925,060 | | 7/1999 | Forber | 606/191 |
| 5,934,284 | | 8/1999 | Plaia et al. | 128/898 |
| 6,136,016 | * | 10/2000 | Barbut et al. | 606/200 |

FOREIGN PATENT DOCUMENTS 0 533 511 A1   7/1992   (EP) .......................... A61M/29/02

* cited by examiner

Primary Examiner—Gary Jackson
Assistant Examiner—Vikki Hoa Trinh
(74) Attorney, Agent, or Firm—Lyon & Lyon LLP

(57) ABSTRACT

An expansion frame system for deploying medical devices in a patient's body cavity. The system typically includes an inner wire disposed within a lumen of an outer wire. Distal ends of the inner and outer wires are attached to a substantially circular frame at first and second points. During use, the outer wire is displaced relative to the inner wire, causing the circular frame to rotate about an axis perpendicular to the line defined by the first and second points. Medical devices, such as a filter, a stent, an occluder or a manometer, can be mounted on the circular frame. The diameter of the expansion frame can be varied to achieve optimal contact with the luminal wall of the body cavity. Methods of using the expansion frame system for temporary or permanent placement of a medical device is disclosed.

42 Claims, 4 Drawing Sheets

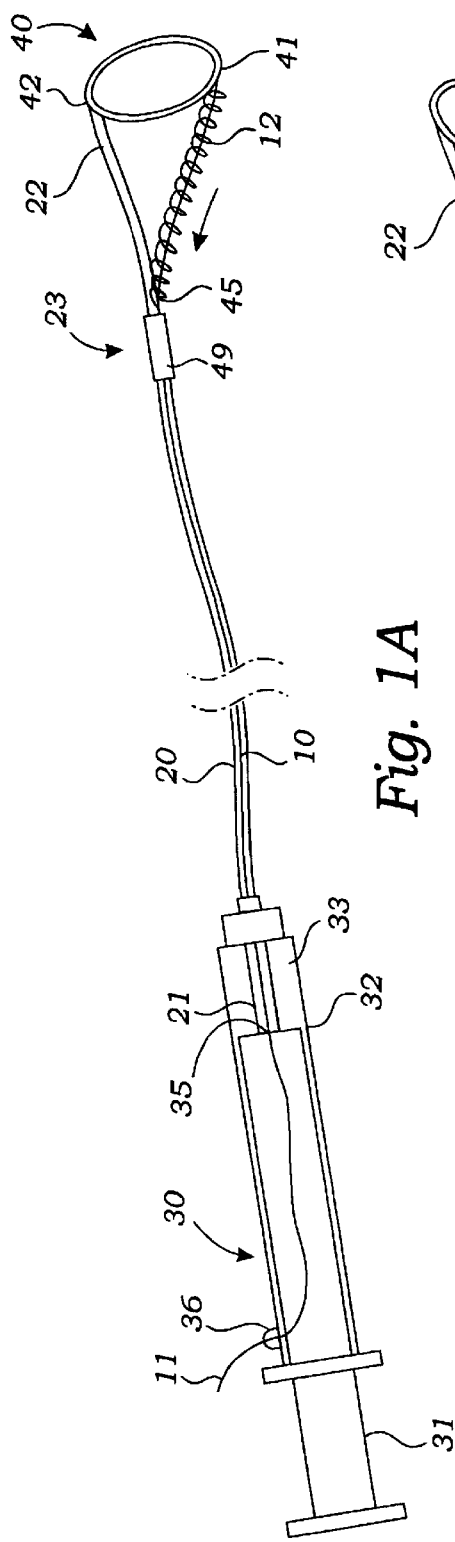
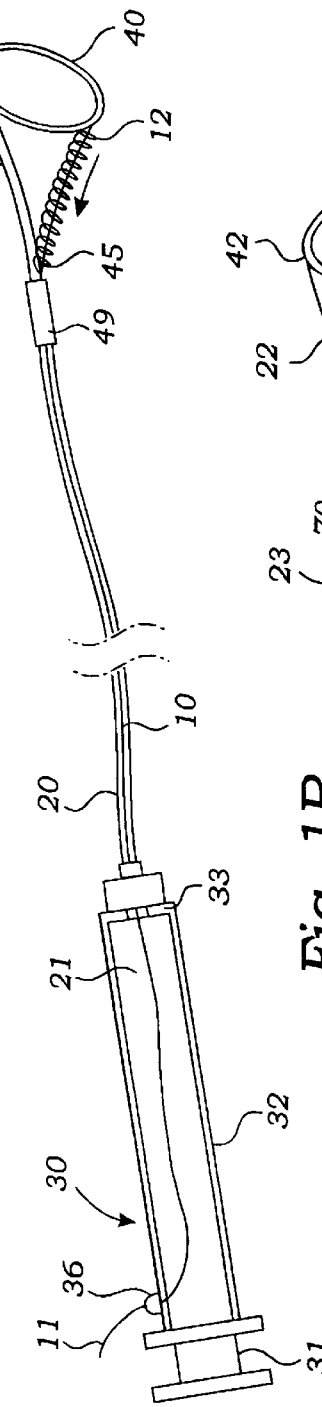
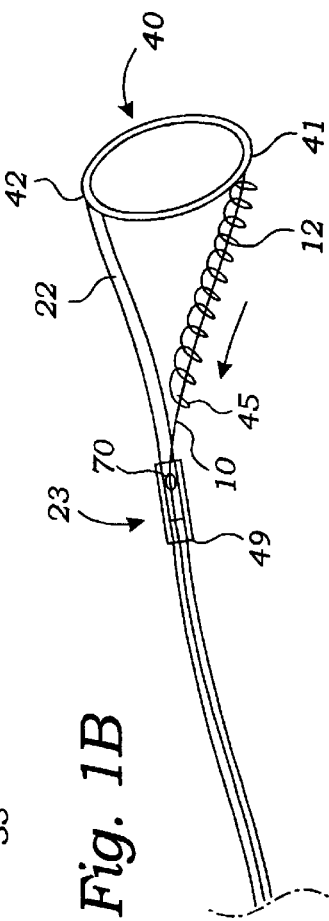
Fig. 1A
Fig. 1B
Fig. 1C

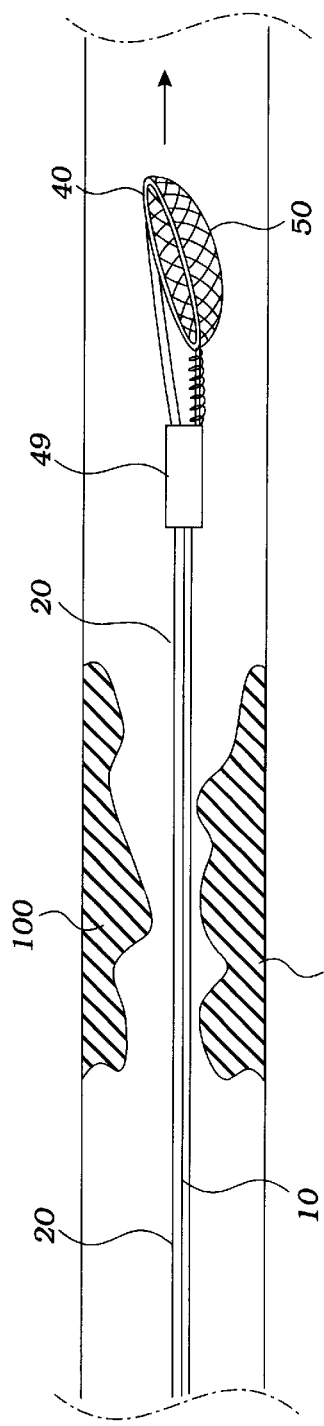
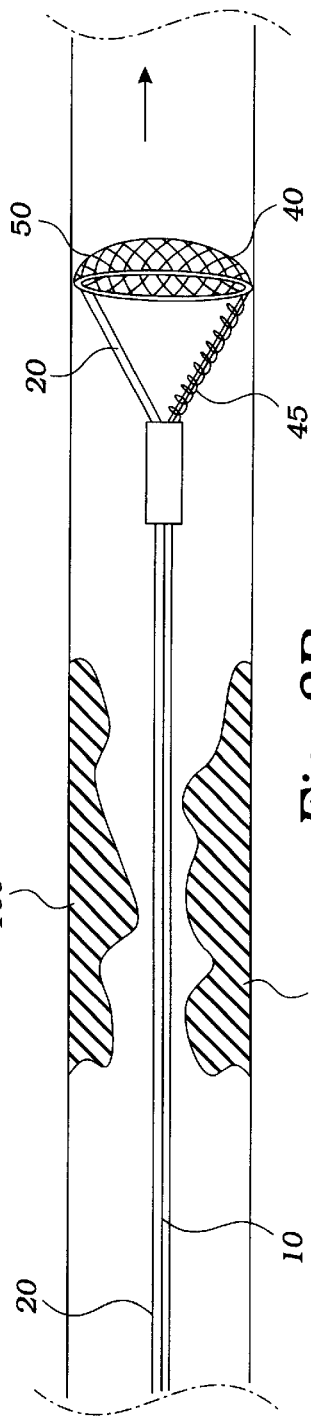
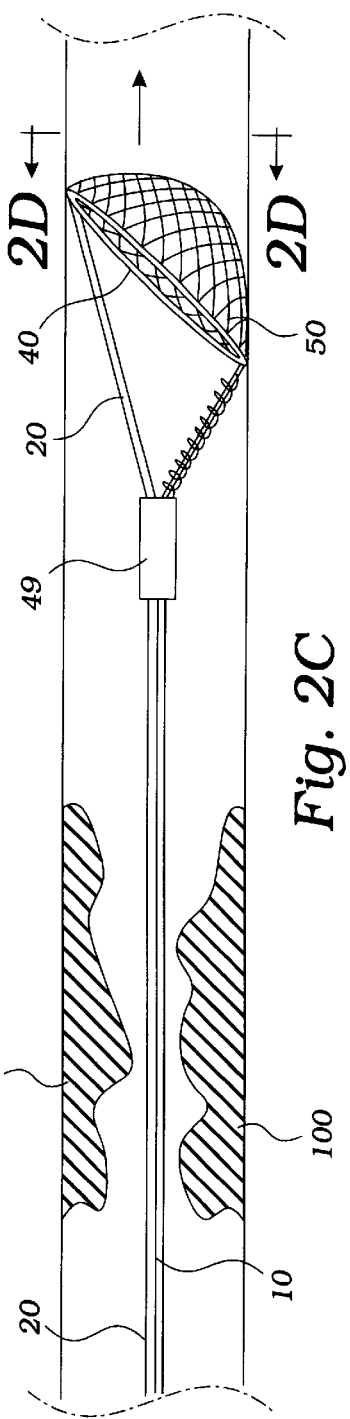
Fig. 2A
Fig. 2B
Fig. 2C

VARIABLE EXPANSION FRAME SYSTEM FOR DEPLOYING MEDICAL DEVICES AND METHODS OF USE

FIELD OF THE INVENTION

The present invention relates generally to systems and methods useful for deploying medical devices within a body, such as a patient's blood vessel. More specifically, the invention provides a variable diameter expansion frame system for temporary or permanent deployment of medical devices, such as a blood filter, a stent, a manometer, or an occluder, in arteries or veins. The frame can be placed in a collapsed condition to facilitate insertion of the device and in an expanded condition to deploy the medical device. The diameter of the frame can be varied to achieve maximal contact with the vascular wall.

BACKGROUND OF THE INVENTION

Treatment of thrombotic or atherosclerotic lesions in blood vessels using the endovascular approach has recently been proven to be an effective and reliable alternative to surgical intervention in selected patients. For example, directional atherectomy and percutaneous translumenal coronary angioplasty (PTCA) with or without stent deployment are useful in treating patients with coronary occlusion. These endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusion iliac vein thrombosis resistant to thrombolysis.

It is well recognized that one of the complications associated with endovascular techniques is the dislodgment of embolic materials which can occur during manipulation of the vessel, thereby causing occlusion of the narrower vessels downstream and ischemia or infarct of the organ which the vessel supplies. There are a number of devices designed to provide blood filtering for entrapment of vascular emboli in arteries. These devices have also been placed prophylactically, e.g., in the inferior vena cava, for prevention of pulmonary embolism in patients with a propensity for thromboembolism.

Filters mounted to the distal end of guidewires have been proposed for intravascular blood filtration. A majority of these devices includes a filter which is attached to a guidewire and is mechanically actuated via struts or a pre-shaped basket which deploys in the vessel. These filters are typically mesh "parachutes" which are attached to the shaft of the wire at the distal end and to wire struts which extend outward in a radial direction on the proximal end. The radial struts open the proximal end of the filter to the wall of the vessel. Blood flowing through the vessel is forced through the mesh thereby capturing embolic material in the filter.

One of the major disadvantages of present filtering devices is that the maximal expansion diameters of the deployed filters are fixed and sometimes fail to optimally and uniformly engage the vascular wall. An operator can only estimate the diameter of the vessel of interest and choose the filter accordingly. If the vessel, e.g., the aorta, is significantly affected by atherosclosis, the actual luminal diameter of the vessel would be over-estimated. In addition to blood filtering devices, this problem is also recognized for deployment of other medical devices, e.g., stents and occluders.

What is needed are simple and safe devices which facilitate placement of other medical devices in a body cavity, such as arteries and veins, and can be variably adjusted to ensure optimal placement of the medical devices. Existing devices are inadequate for this purpose.

SUMMARY OF THE INVENTION

The present invention provides devices and methods for temporary placement of medical devices, including a filter, an occluder, and a stent in a body cavity. More specifically, the invention provides a expansion frame system, the diameter of which can be variably adjusted to facilitates, for example, insertion of blood filter for capturing embolic material in an artery or vein.

In one embodiment, the expansion frame system includes an outer wire, an inner wire, and a circular or elliptical frame. The outer wire has a lumen communicating with a proximal end and a distal end, and is adapted to receive a percutaneous endovascular medical instrument. The inner wire, having a proximal end and a distal end, is disposed within the lumen of the outer wire. The distal ends of the inner and outer wires are attached, respectively, to the frame at first and second circumferential points at approximately 180° from each other. The proximal ends of the inner and outer wires can be manipulated so that the outer wire can be displaced relative to the inner wire, causing the frame to rotate about an axis perpendicular to the line defined by the first and second circumferential points. In this way, the frame can be placed in a collapsed or an expanded condition.

In another embodiment, the expansion frame system further includes a force biasing element, such as a spring, disposed about the distal end of the inner wire. The distal region of the outer wire has an opening, through which the inner wire passes to attach to the circular or elliptical frame. The biasing element is capable of biasing the second circumferential point of the circular frame away from the opening of the outer wire.

In still another embodiment, the expansion frame system includes a syringe having a barrel and a plunger, where the outer wire is housed within a lumen of the barrel and is mounted on a distal surface of the plunger. The proximal end of the inner wire passes through the distal surface of the plunger and is mounted on the barrel. When the plunger is advanced slideably in the lumen of the barrel, the outer wire is displaced relative to the inner wire, causing the frame to rotate about an axis perpendicular to the line defined by the first and second circumferential points. In other embodiments, the proximal end of the barrel includes a locking mechanism, capable of fixing the displacement of the plunger relative to the barrel.

In certain embodiments, an occluding device, such as a non-permeable membrane, is mounted on the frame. When in use, the membrane provides isolation of blood flow in a vessel, e.g., isolation of aortic blood flow during cardiopulmonary bypass. In other embodiments, a filtering device, e.g., a parachute, basket, or scroll, is mounted on the frame, and a mesh is disposed over the frame. The filtering device may include an inflation seal for achieving better contact with the vascular walls. The construction and use of an associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30 1996, Barbut et al., U.S. application Ser. No.

08/645,762, filed May 14, 1996, and, Barbut et al., U.S. Pat. No. 5,662,671, and the contents of each of these prior applications are expressly incorporated herein by reference.

The methods of the present invention are useful for deploying a medical device within a body cavity for, e.g., protecting a patient from embolization during an endovascular procedure. The expansion frame system can be inserted to capture plaque and/or thrombi from the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The expansion frame system can be used prophylactically in patients with hypercoagulable state, including protein C or protein S deficiency, to prevent pulmonary embolism. It can also be used during an endovascular procedure to prevent distal embolization of thrombi and/or foreign bodies in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of using the expansion frame system, the frame, in a collapsed condition, is inserted percutaneously or through an incision into a patient's body cavity, and is advanced into a region of interest. The proximal end of the outer wire is retracted relative to the proximal end of the inner wire, causing the frame to rotate about an axis perpendicular to the line defined by the first and second points, thereby increasing its profile. In this way, the frame circumferentially engages the luminal wall.

When used during an endovascular procedure, e.g., percutaneous transluminal angioplasty of a coronary or carotid artery, to provide protection against distal embolization, the expansion frame system, having a filter mounted on the frame in a collapsed condition, is inserted through a peripheral artery into the coronary or carotid artery distal to the occluding lesion. In using the embodiments which include a syringe, the plunger is depressed distally against the barrel, thereby retracting the proximal end of the outer wire relative to the inner wire, and placing the frame in a collapsed condition. After the frame is positioned downstream from the occluding lesion, the plunger is released, moving proximally within the barrel of the syringe, thereby distancing the proximal end of the outer wire relative to the inner wire, and placing the frame in an expanded condition. The contact between the circumference of the frame and the luminal wall of the artery is variably adjusted to obtain optimal contact.

The angioplasty catheter carrying the angioplasty balloon at a distal end is inserted into the artery, over the outer wire in certain embodiments, and the balloon is inflated to dilate the stenotic vascular lumen. Embolic debris generated during the angioplasty procedure are captured by the filter mounted on the expansion frame. After adequate luminal diameter is re-established for coronary blood flow, the expansion frame with the entrapped emboli is collapsed by depressing the plunger against the barrel of the syringe, and removed from the artery.

It will be understood that there are several advantages in using the variable diameter expansion frame disclosed herein for deploying a medical device. For example, the expansion frame system (1) can be used to deploy a variety of medical devices, including a filter, stent, and an occluder, (2) can withstand high arterial blood flow for an extended time, (3) can be used to deploy a variety of blood filters, particularly suited for temporary filtration of blood in any vessel to entrap embolic debris, thereby minimizing neurologic, cognitive, and cardiac complications associated with distal embolization, (4) can be used with any endovascular catheter with or without an imaging device, (5) can be inserted into vessels or a body cavity of various diameter, (6) can be variably adjusted to achieve optimal contact between the frame and the inner wall of a vessel or body cavity, and (7) can be used in adult and pediatric patients.

BRIEF DESCRIPTION OF THE DRAWINGS

FIG. 1A depicts an embodiment of an expansion frame system including a syringe according to the present invention.

FIG. 1B depicts the expansion frame system of FIG. 1A having a frame in a collapsed condition.

FIG. 1C depicts the expansion frame system of FIG. 1A showing the mechanism within tubular member 49.

FIG. 2A depicts the expansion frame system of FIG. 1B carrying a filter in a collapsed condition inserted in a vessel.

FIG. 2B depicts the expansion frame system of FIG. 2A deploying the filter in a vessel.

FIG. 2C depicts the expansion frame system of FIG. 2A deploying the filter in another vessel having a smaller diameter.

DETAILED DESCRIPTION

Figure 2D:
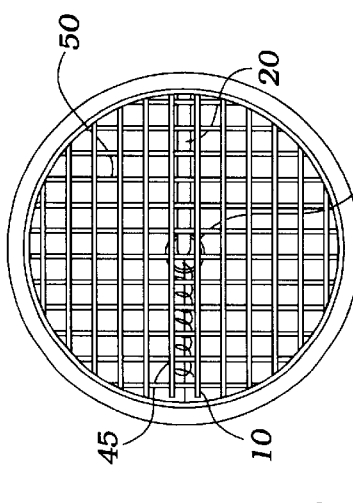
FIG. 2D depicts a distal view of the expansion frame system of FIG. 2C.

Although the variable expansion frame system is most useful in deploying blood filters in a patient's blood vessel as disclosed herein, it will be understood that the system can also be used to deploy a variety of other medical devices, e.g., a stent, an occluder, an endoscopic imaging device, or a manometer, in various body cavities.

In a first embodiment, the expansion frame system includes inner wire 10, outer wire 20, syringe 30, and substantially circular frame 40 as depicted in FIGS. 1A and 1B. Outer wire 20 has proximal end 21, distal end 22 and lumen 25. Inner wire 10, having proximal end 11 and distal end 12, is disposed within lumen 25 of the outer wire. Distal end 12 of the inner wire and distal end 22 of the outer wire are attached, respectively, to frame 40 at circumferential point 41 and circumferential point 42. The frame is substantially circular or elliptical. Point 41 is disposed approximately 180° from point 42. In certain embodiments, point 41 is disposed approximately 30°, 45°, 60°, 90°, 120°, 135°, or any other suitable angles from point 42. Distal region 23 of outer wire 20 has an opening 70 (FIG. 1C) through its wall, which is enclosed in tubular member 49 and allows inner wire 10 to pass through. Spring 45, a force biasing element, is disposed about distal end 12 of inner wire 10, thereby biasing point 41 away from the opening of the outer wire. Syringe 30 comprises plunger 31 slideably inserted in lumen 33 of barrel 32. Proximal end 21 of outer wire 20 is mounted on distal surface 35 of the plunger. Proximal end 11 of inner wire 10 passes through distal surface 35 of the plunger and is mounted on attachment 36 of the barrel.

In use, as depicted in FIG. 1B, frame 40 is collapsed by advancing plunger 31 distally relative to barrel 32, thereby retracting proximal end 21 of the outer wire relative to proximal end 11 of the inner wire, and causing frame 40 to rotate about an axis perpendicular to the line defined by points 41 and 42. Medical devices mounted or carried on frame 40 are placed in a collapsed condition to facilitate insertion into a body cavity. The displacement between plunger 31 and barrel 32 may be fixed by a locking mechanism included in a proximal end of the syringe. When frame 40 is positioned in the region of interest, plunger 31 is withdrawn, thereby placing frame 40 in an expanded condition and deploying the medical device. The diameter of the substantially circular frame can be varied by adjusting the displacement between the proximal end of the outer wire relative to the inner wire. In certain embodiments, a radiopaque marker may be mounted on frame 40, tubular member 49, or distal regions of the inner and/or the outer wire for verifying the position of the deployed device.

The expansion frame system of FIG. 1B is inserted in an artery distal to atheromatous occlusion 100 as depicted in FIG. 2A. A filter, having mesh 50 is mounted on frame 40. The frame is placed in a collapsed condition to facilitate insertion through the stenotic vascular lesion. In FIG. 2B, when the filter is positioned downstream from occlusion 100, frame 40 is rotated by retracting the proximal end of outer wire 20 relative to inner wire 10, thereby circumferentially engaging the luminal wall and expanding the filter in the artery. The diameter of frame 40 can be varied by adjusting the displacement between a proximal end of the outer wire relative to the inner wire to maximally engage the frame with the vascular wall. Endoscopic procedures, including atherectomy, angioplasty, and/or stenting, can be performed on the occlusion. Embolic materials, such as calcium, atheromatous plaque, tissue debris, and/or thrombi, are captured by mesh 50 of the filter. After adequate luminal size is achieved after the procedures, blood flow is re-established to push the embolic material toward mesh 50 and to perfuse distal organs. After completion of the procedure, the endovascular device is withdrawn. Frame 40 and the filter with the captured embolic debris are collapsed and removed from the vessel.

In situations where the luminal diameter of the vessel is overestimated, i.e., the diameter of the frame exceeding the luminal diameter, frame 40 can be adjusted to achieve maximal contact with the vessel wall as depicted in FIG. 2C. FIG. 2D depicts a distal view of frame 40 with mesh 50.

By way of example, when the filter as disclosed herein is intended for use in the aorta, the area of the mesh required for the device is calculated from Bernoulli's equation as described in our earlier applications including Barbut et al., U.S. application Serial No., U.S. application Serial No. 08/553,137, filed Nov. 7, 1995, Barbut et al., U.S. application Serial No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996.

In an embodiment of the filter that is to be used in the aorta, mesh with dimensions within the following ranges is desirable: mesh area is 0.004–5 in$^2$, more preferably 0.007–4 in$^2$, more preferably 0.010–3 in$^2$, more preferably 0.015–2 in$^2$, more preferably 0.020–1 in$^2$, more preferably 0.025–0.076 in$^2$; mesh thickness is 60–280 $\mu$m, more preferably 70–270 $\mu$m, more preferably 80–260 $\mu$m, more preferably 90–250 $\mu$m, more preferably 100–250 $\mu$m, more preferably 120–230 $\mu$m, more preferably 140–210 $\mu$m; thread diameter is 30–145 $\mu$m, more preferably 40–135 $\mu$m, more preferably 50–125 $\mu$m, more preferably 60–115 $\mu$m, more preferably 70–105 $\mu$m, and pore size is 500 $\mu$m or less, more preferably 400 $\mu$m or less, more preferably 300 $\mu$m or less, more preferably 200 $\mu$m or less, more preferably 100 $\mu$m or less, more preferably 50 $\mu$m or less and usually larger than at least a red blood cell. In a preferred embodiment of the invention, mesh area is 2–8 in$^2$, mesh thickness is 60–200 $\mu$m, thread diameter is 30–100 $\mu$m, and pore size is 50–300 $\mu$m. In a further preferred embodiment of the invention, mesh area is 3–5 in$^2$, mesh thickness is 60–150 $\mu$m, thread diameter is 50–80 $\mu$m, and pore size is 100–250 $\mu$m.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded or adhesive bonded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

Figure 3A:
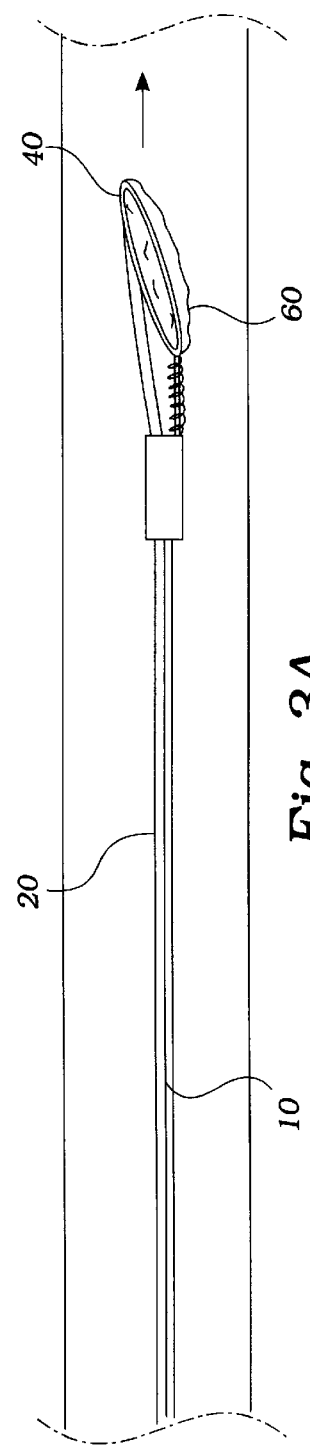
FIG. 3A depicts the expansion frame system of FIG. 1B carrying a membrane inserted in a vessel.
Figure 3B:
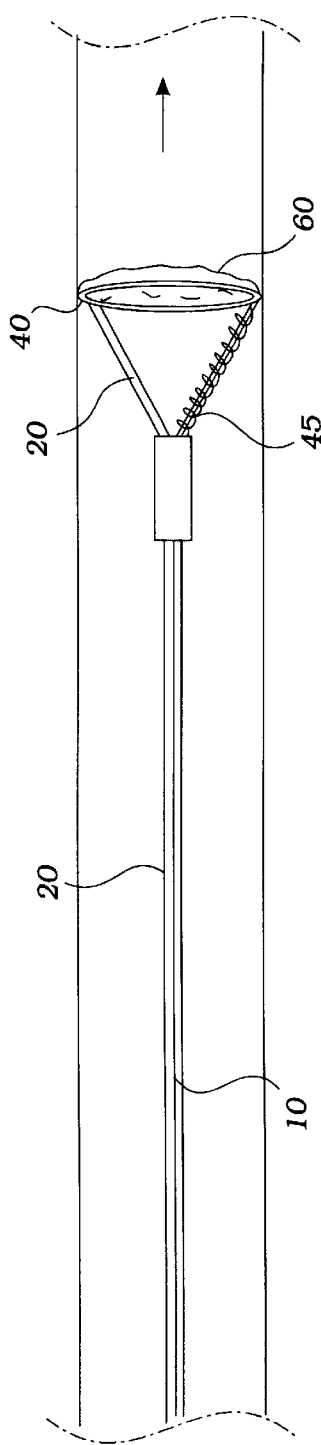
FIG. 3B depicts the expansion frame system of FIG. 3A deploying the membrane in the vessel.

The expansion frame system can be used to deploy other devices, such as non-permeable membrane 60, as depicted in FIGS. 3A and 3B. In FIG. 3A, membrane 60 is mounted on frame 40, which is placed in a collapsed condition by retracting a proximal end of outer wire 20 relative to inner wire 10. When the membrane is positioned within a region of interest in a vessel, frame is rotated to circumferentially engage the luminal wall. When deployed in the ascending aorta during cardiopulmonary bypass, the nonpermeable membrane provides circulatory isolation of the coronary blood flow from the peripheral vascular system.

Figure 4:
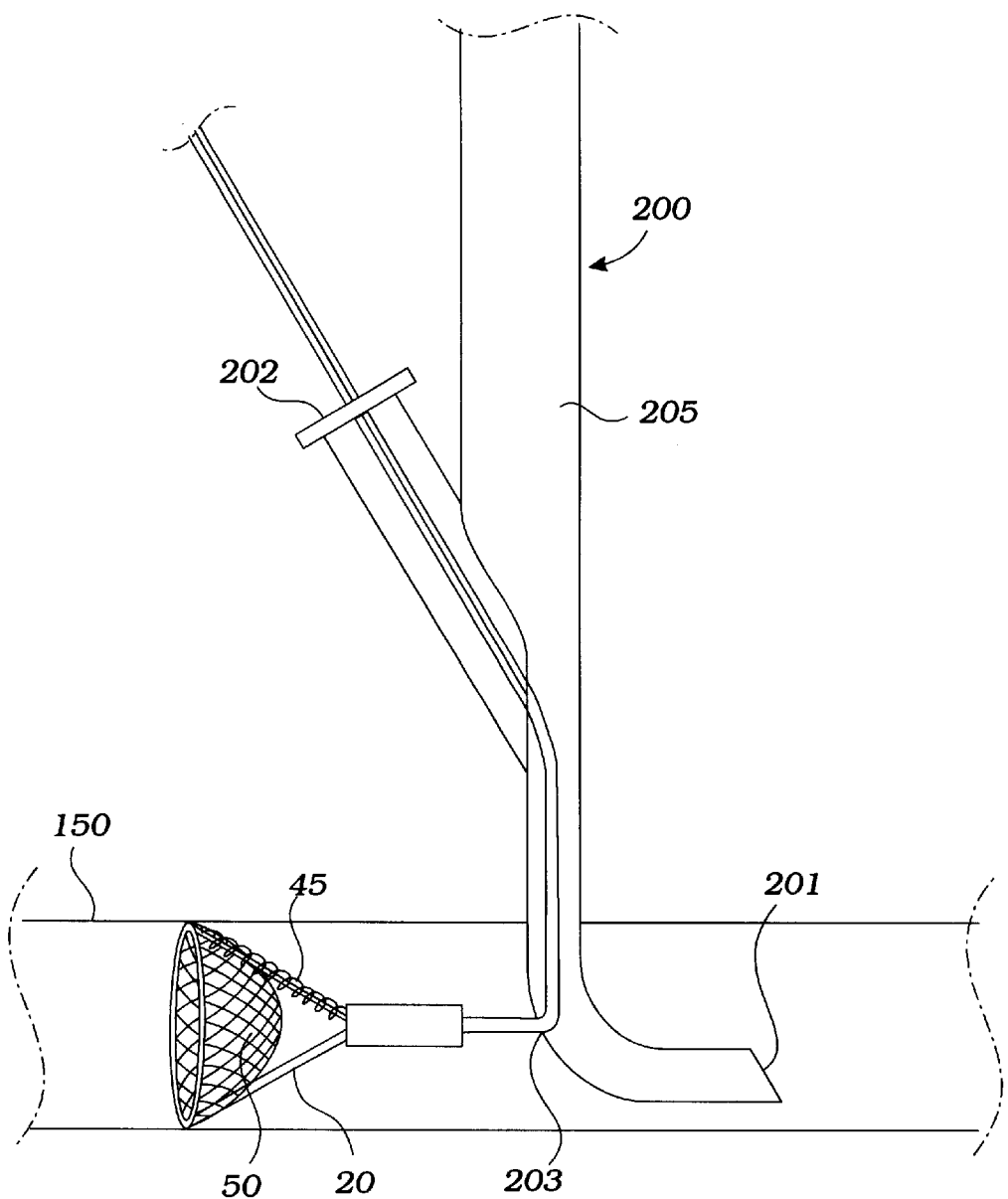
FIG. 4 depicts an expansion frame system carrying a filter deployed in the aorta through a side port of a cannula.

In other embodiments, the expansion frame system can be used to deploy a filter or any other device directly into the aorta through a cannula having a side port as described in Maahs, U.S. Pat. No. 5,846,260, incorporated herein by reference in its entirety. In FIG. 4, the expansion frame system carrying a filter having mesh 50 is inserted through side port 202 of cannula 200. Cannula 200 includes lumen 205 which communicates with perfusion port 201. The lumen communicating with side port 202 may communicate with lumen 205, or in other embodiments remains separate and isolated from lumen 205. When the cannula is inserted into aorta 150 during cardiopulmonary bypass, for example, port 201 is positioned downstream in the aorta to perfuse peripheral organs. The filter is deployed upstream in the aorta through port 203 of the cannula to capture any embolic material generated during cardiothoracic procedures. In still other embodiments, the expansion frame system can be used through any vascular introducer, such as those described in Martinez et al., U.S. application Ser. No. 09/365,650, entitled MODULAR ACCESS PORT FOR DEVICE DELIVERY, filed Aug. 2, 1999, incorporated herein by reference in its entirety.

The length of the inner and outer wire will generally be between 30 and 300 centimeters, preferably approximately between 50 and 180 centimeters. The inner diameter of the lumen of the outer wire will generally be between 0.05 and 0.5 centimeters, preferably approximately between 0.1 and 0.25 centimeters. The diameter of the expansion frame will be capable of expansion to an outer diameter of at least 0.3 cm, more preferably at least 1.5 cm, more preferably at least 2 cm, more preferably at least 2.5 cm, more preferably at least 3 cm, more preferably at least 3.5 cm, more preferably at least 4 cm, more preferably at least 4.5 cm, more preferably at least 5 cm, more preferably at least 5.5 cm, more preferably at least 6 cm. These ranges cover suitable diameters for both pediatric use and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be apparent that certain features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

What is claimed is:

1. A variable diameter expansion frame, comprising:
   an outer wire having a proximal end, a distal end, and a lumen therebetween;
   an inner wire having a proximal end and a distal end, the inner wire being disposed within the lumen of the outer wire, the inner wire slideable relative to the outer wire; and
   a substantially circular frame attached at a first circumferential point to the distal end of the outer wire, and attached at a second circumferential point to the distal end of the inner wire, the first circumferential point being disposed approximately 180° from the second circumferential point,
   wherein, during use, the outer wire is displaced relative to the inner wire, and the circular frame is caused to rotate about an axis perpendicular to the line defined by the first and second circumferential points.

2. The expansion frame of claim 1, wherein the outer wire has a hole through its wall near the distal end, and wherein the inner wire passes through the hole in the outer wire.

3. The expansion frame of claim 2, further comprising a force biasing element disposed about the distal end of the inner wire and biasing the second circumferential point of the circular frame away from the hole of the outer wire.

4. The expansion frame of claim 3, wherein the force biasing element is a spring.

5. The expansion frame of claim 1, further comprising a filter mesh disposed about the circular frame.

6. The expansion frame of claim 1, further comprising an impermeable membrane disposed about the circular frame.

7. The expansion frame of claim 1, further comprising a syringe having a barrel and a plunger, wherein the proximal end of the inner wire passes through a distal surface of the plunger and is mounted on the barrel.

8. The expansion frame of claim 7, wherein the outer wire is mounted on the distal surface of the plunger.

9. The expansion frame of claim 7, further comprising a locking mechanism capable of fixing the displacement between the plunger and the barrel.

10. The expansion frame of claim 1, further comprising an angioplasty catheter adapted to receive and be guided by the outer wire of the expansion frame.

11. The expansion frame of claim 1, further comprising a stent deployment catheter adapted to receive and be guided by the outer wire of the expansion frame.

12. The expansion frame of claim 1, further comprising an atherectomy catheter adapted to receive and be guided by the outer wire of the expansion frame.

13. The expansion frame of claim 1, further comprising an imaging catheter adapted to receive and be guided by the outer wire of the expansion frame.

14. A method for deploying a medial device within a body, comprising the steps of:
   providing an expansion frame comprising an outer wire, an inner wire, and a substantially circular frame attached at a first point to a distal end of the outer wire, and attached at a second point to a distal end of the inner wire, the inner wire being disposed within the lumen of the outer wire, the inner wire slideable relative to the outer wire;
   introducing the expansion frame into a lumen within the body of a patient;
   advancing the expansion frame to a region of interest; and
   retracting a proximal end of the outer wire relative to a proximal end of the inner wire,
   wherein the circular frame rotates about an axis perpendicular to the line defined by the first and second point, and the circular frame thereby circumferentially engages the luminal wall.

15. The method of claim 14, wherein the expansion frame further comprises a filter mesh disposed about the circular frame.

16. The method of claim 14, wherein the expansion frame further comprises an impermeable membrane disposed about the circular frame.

17. The method of claim 14, wherein the lumen is a vessel.

18. The method of claim 17, wherein the vessel is an artery.

19. An expansion frame system, comprising:
   a cannula having a proximal end, a distal end, a first lumen therebetween, and a side port communicating with a second lumen which extends to the distal end of the cannula; and
   a variable diameter expansion frame comprising an outer wire having a proximal end and a distal end, an inner wire having a proximal end and a distal end, the inner wire being disposed within the lumen of the outer wire, the inner wire slideable relative to the outer wire, and a substantially circular frame attached at a first circumferential point to the distal end of the outer wire, and attached at a second circumferential point to the distal end of the inner wire, the first circumferential point being disposed approximately 180° from the second circumferential point,
   wherein, during use, the expansion frame is advanced through the side port of the cannula and is deployed within the lumen of a vessel.

20. The method of claim 18, wherein the artery is an aorta.

21. The method of claim 18, wherein the artery is a carotid artery.

22. The method of claim 14, further comprising the step of performing an endoluminal procedure upstream of the expansion frame.

23. The method of claim 22, wherein embolic materials are dislodged during the procedure and captured by the expansion frame.

24. The method of claim 14, wherein the expansion frame is introduced through an incision by direct access.

25. The method of claim 14, wherein the expansion frame is introduced percutaneously.

26. The method of claim 14, wherein a radiopaque marker is mounted on the circular frame.

27. The method of claim 14, further comprising the step of verifying the position of the frame using fluoroscopy.

28. The method of claim 22, wherein the endoluminal procedure is performed by advancing an endoluminal instrument over the outer wire.

29. The method of claim 28, wherein the endoluminal instrument is an angioplasty catheter adapted to receive and be guided by the outer wire of the expansion frame.

30. The method of claim 28, wherein the endoluminal instrument is a stent deployment catheter adapted to receive and be guided by the outer wire of the expansion frame.

31. The method of claim 28, wherein the endoluminal instrument is an atherectomy catheter adapted to receive and be guided by the outer wire of the expansion frame.

32. The method of claim 28, wherein the endoluminal instrument is an imaging catheter adapted to receive and be guided by the outer wire of the expansion frame.

33. The method of claim 30, wherein the stent deployment catheter comprises:

a self-expanding stent disposed about the outer wire; and a sheath disposed about the stent, wherein the sheath is retracted to release the stent.

34. The method of claim 17, wherein the step of introducing the expansion frame into the vessel comprises advancing the expansion frame through an introducer.

35. The method of claim 34, wherein the introducer comprises a cannula.

36. The method of claim 34, wherein the introducer is a port on a cannula.

37. The method of claim 36, wherein the port is separate from a lumen of the cannula.

38. The expansion frame of claim 19, wherein during use, the outer wire is displaced relative to the inner wire and the circular frame is caused to rotate about an axis perpendicular to the line defined by the first and second circumferential points.

39. The expansion frame of claim 19, wherein the second lumen communicates with the first lumen.

40. The expansion frame of claim 19, wherein the cannula is an arterial cannula.

41. The expansion frame of claim 19, wherein the side port further comprises a hemostatic valve.

42. The expansion frame of claim 19, wherein the second lumen is separate from the first lumen and communicates at a distal end with a port.

* * * * *